United States Patent
Wolfson et al.

(10) Patent No.: US 9,675,441 B2
(45) Date of Patent: Jun. 13, 2017

(54) PROSTHESIS FOR SIMULATING NATURAL KINEMATICS

(71) Applicant: Biomet UK Limited, Bridgend (GB)

(72) Inventors: David Wolfson, Leeds (GB); Russell Lloyd, Wiltshire (GB); John Joseph O'Connor, Oxford (GB); Mohammed Imran Khan, Berkshire (GB); David Wycliffe Murray, Oxford (GB); Christopher Alexander Dodd, Oxford (GB); John William Goodfellow, Oxford (GB)

(73) Assignee: Biomet UK Limited (GB)

( * ) Notice: Subject to any disclaimer, the term of this patent is extended or adjusted under 35 U.S.C. 154(b) by 0 days.

(21) Appl. No.: 14/666,614

(22) Filed: Mar. 24, 2015

(65) Prior Publication Data
US 2015/0196387 A1 Jul. 16, 2015

Related U.S. Application Data

(63) Continuation of application No. 13/923,768, filed on Jun. 21, 2013, now Pat. No. 8,998,993, which is a
(Continued)

(30) Foreign Application Priority Data

Nov. 2, 2007 (GB) .................................. 0721610.4
Apr. 1, 2008 (GB) .................................. 0805917.2

(51) Int. Cl.
*A61F 2/38* (2006.01)
*A61F 2/08* (2006.01)
*A61F 2/30* (2006.01)

(52) U.S. Cl.
CPC .......... *A61F 2/0811* (2013.01); *A61F 2/3094* (2013.01); *A61F 2/38* (2013.01);
(Continued)

(58) Field of Classification Search
CPC .... A61F 2/3836; A61F 2/3868; A61F 2/3094; A61F 2/0811; A61F 2/38; A61F 2002/3863; A61F 2/3859
(Continued)

(56) References Cited

U.S. PATENT DOCUMENTS

| 2,663,837 A | 12/1953 | Krings |
| 3,932,045 A | 1/1976 | Hillberry et al. |

(Continued)

FOREIGN PATENT DOCUMENTS

| BE | 1008201 A3 | 2/1996 |
| EP | 0330328 A1 | 8/1989 |

(Continued)

OTHER PUBLICATIONS

International Search Report mailed Jul. 27, 2009 for PCT/GB2008/003677 filed Oct. 31, 2008, of which the current case (U.S. Appl. No. 12/740,998) claims benefit. PCT/GB2008/003677 claims benefit of GB App. 0721610,4, filed Nov. 2, 2007 and GB App. 0805917.2, filed Apr. 1, 2008.
(Continued)

*Primary Examiner* — Alvin Stewart
(74) *Attorney, Agent, or Firm* — Schwegman Lundberg & Woessner, P.A.

(57) ABSTRACT

A bearing component 2 for a joint replacement prosthesis comprises a first bearing element 4; a second bearing element 6, and a linking element 8, operatively connecting the first and second bearing elements 4, 6 and permitting relative motion there between. The flexible linking element 8 prevents dislocation of mobile bearings in a total knee replacement prosthesis. The invention also relates to a bridging element which retains the linking element 8 with some play, which acts as a ligament support 2051, and which causes a deflection of the line of action of a ligament 1018. A joint replacement prosthesis is also disclosed comprising a biasing element 1140 or a tensioning element 1220 operatively coupled to the artificial ligament 1018. The biasing element 1140 or tensioning element 1220 may be housed in the stem of a tibia tray 1006.

20 Claims, 17 Drawing Sheets

Figure 1:
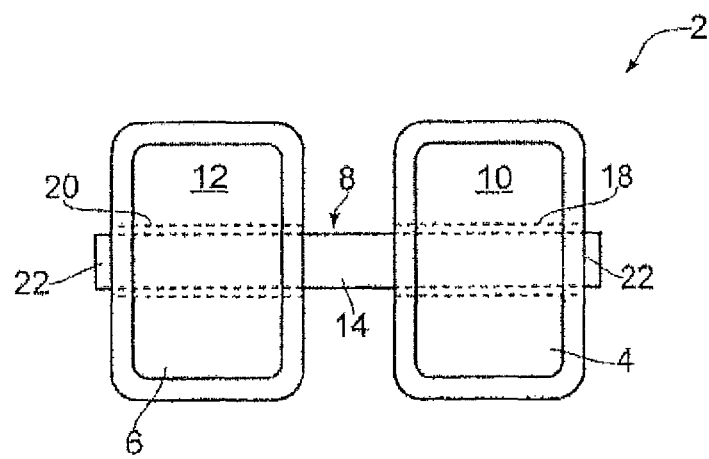

Related U.S. Application Data continuation of application No. 13/923,779, filed on Jun. 21, 2013, now Pat. No. 9,381,079, said application No. 13/923,768 is a continuation of application No. 12/740,998, filed as application No. PCT/GB2008/003677 on Oct. 31, 2008, now Pat. No. 8,470,048.

(52) U.S. Cl.
 CPC .......... *A61F 2/3836* (2013.01); *A61F 2/3868* (2013.01); *A61F 2/08* (2013.01); *A61F 2002/0847* (2013.01); *A61F 2002/30462* (2013.01); *A61F 2002/30466* (2013.01); *A61F 2220/0075* (2013.01); *Y10T 29/49707* (2015.01)

(58) Field of Classification Search
 USPC .......... 623/20.14–20.36, 18.11, 20.11–20.13, 623/16.11, 21.11–21.18
 See application file for complete search history.

(56) References Cited

U.S. PATENT DOCUMENTS

| | | | |
|---|---|---|---|
| 3,946,446 A | 3/1976 | Schofield | |
| 4,207,627 A | 6/1980 | Cloutier | |
| 4,267,608 A | 5/1981 | Bora, Jr. | |
| 4,711,639 A | 12/1987 | Grundei | |
| 4,714,475 A | 12/1987 | Grundei et al. | |
| 4,744,793 A | 5/1988 | Parr et al. | |
| 4,770,663 A | 9/1988 | Hanslik et al. | |
| 4,828,562 A | 5/1989 | Kenna | |
| 5,151,104 A | 9/1992 | Kenna | |
| 5,282,867 A | 2/1994 | Mikhail | |
| 5,282,868 A | 2/1994 | Bahler | |
| 5,395,401 A | 3/1995 | Bahler | |
| 5,470,354 A | 11/1995 | Hershberger et al. | |
| 5,507,812 A | 4/1996 | Moore | |
| 5,534,033 A | 7/1996 | Simpson | |
| 5,824,104 A | 10/1998 | Tuke | |
| 5,967,790 A | 10/1999 | Strover et al. | |
| 5,993,486 A | 11/1999 | Tomatsu | |
| 6,004,351 A | 12/1999 | Tomita et al. | |
| 6,036,694 A | 3/2000 | Goble et al. | |
| 6,165,223 A | 12/2000 | Metzger et al. | |
| 6,190,411 B1 | 2/2001 | Lo et al. | |
| 6,217,618 B1 | 4/2001 | Hileman | |
| 6,299,646 B1 | 10/2001 | Chambat et al. | |
| 6,319,283 B1 | 11/2001 | Insall et al. | |
| 6,361,564 B1 | 3/2002 | Marceaux et al. | |
| 6,406,497 B2 | 6/2002 | Takei | |
| 6,413,279 B1 | 7/2002 | Metzger et al. | |
| 6,592,622 B1 | 7/2003 | Ferguson | |
| 6,620,198 B2 | 9/2003 | Burstein et al. | |
| 6,905,513 B1* | 6/2005 | Metzger ..................... | A61F 2/08 623/20.14 |
| 6,972,039 B2 | 12/2005 | Metzger et al. | |
| 7,060,101 B2 | 6/2006 | O'Connor et al. | |
| 7,153,327 B1 | 12/2006 | Metzger | |
| 7,255,715 B2 | 8/2007 | Metzger | |
| 7,615,054 B1 | 11/2009 | Bonutti | |
| 7,655,041 B2 | 2/2010 | Clifford et al. | |
| 7,887,586 B2 | 2/2011 | Linares | |
| 7,998,203 B2 | 8/2011 | Blum | |
| 8,066,776 B2 | 11/2011 | O'Connor et al. | |
| 8,137,382 B2 | 3/2012 | Denham et al. | |
| 8,163,016 B2 | 4/2012 | Linares | |
| 8,177,840 B2 | 5/2012 | Linares | |
| 8,470,048 B2* | 6/2013 | Wolfson ................ | A61F 2/3836 623/20.15 |
| 8,496,704 B2 | 7/2013 | Lenz et al. | |
| 8,500,818 B2 | 8/2013 | Metzger et al. | |
| 8,808,374 B2 | 8/2014 | Eggli | |
| 8,858,642 B2 | 10/2014 | Metzger et al. | |
| 8,888,856 B2 | 11/2014 | Byrd et al. | |
| 8,998,993 B2* | 4/2015 | Wolfson ................ | A61F 2/3836 623/18.11 |
| 9,381,079 B2* | 7/2016 | Wolfson ................ | A61F 2/3836 |
| 9,433,494 B2 | 9/2016 | Wolfson et al. | |
| 2002/0010512 A1 | 1/2002 | Takei | |
| 2004/0117014 A1 | 6/2004 | Bryant | |
| 2004/0193279 A1 | 9/2004 | Roger | |
| 2005/0065533 A1 | 3/2005 | Magen et al. | |
| 2005/0070906 A1 | 3/2005 | Clark et al. | |
| 2005/0187635 A1 | 8/2005 | Metzger | |
| 2006/0004460 A1 | 1/2006 | Engh et al. | |
| 2010/0305698 A1 | 12/2010 | Metzger et al. | |
| 2010/0305709 A1 | 12/2010 | Metzger et al. | |
| 2011/0015749 A1 | 1/2011 | Engh et al. | |
| 2011/0106265 A1* | 5/2011 | Wolfson ................ | A61F 2/3836 623/18.11 |
| 2013/0011025 A1 | 1/2013 | Liu et al. | |
| 2013/0282130 A1* | 10/2013 | Wolfson ................ | A61F 2/3836 623/20.14 |
| 2013/0297020 A1* | 11/2013 | Wolfson ................ | A61F 2/3836 623/13.13 |
| 2014/0067075 A1 | 3/2014 | Makower et al. | |
| 2014/0172097 A1 | 6/2014 | Clifford et al. | |
| 2014/0222149 A1 | 8/2014 | Amis et al. | |
| 2014/0249627 A1 | 9/2014 | Linder-Ganz et al. | |
| 2014/0296980 A1 | 10/2014 | Gedet et al. | |
| 2014/0316526 A1 | 10/2014 | Grotz | |
| 2015/0196386 A1* | 7/2015 | Wolfson ................ | A61F 2/3836 623/13.14 |
| 2015/0196387 A1* | 7/2015 | Wolfson ................ | A61F 2/3836 623/13.13 |
| 2016/0120639 A1* | 5/2016 | Murray ................ | A61F 2/389 623/13.12 |
| 2016/0193033 A1* | 7/2016 | Murray ................ | A61F 2/0811 623/13.12 |

FOREIGN PATENT DOCUMENTS

| | | | |
|---|---|---|---|
| EP | 0376641 A1 | 7/1990 | |
| EP | 0413549 A2 | 2/1991 | |
| EP | 0425140 A2 | 5/1991 | |
| EP | 1797845 A1 | 6/2007 | |
| FR | 2663837 A1 | 1/1992 | |
| GB | 2312168 A | 10/1997 | |
| GB | 2403416 A | 1/2005 | |
| GB | 2454251 A | 5/2009 | |
| GB | 2458918 A | 10/2009 | |
| GB | 2464639 A | 4/2010 | |
| GB | 2464862 A | 5/2010 | |
| GB | 2474394 A | 4/2011 | |
| GB | 2491997 A | 12/2012 | |
| GB | 2495042 A | 3/2013 | |
| JP | 01274757 A | 11/1999 | |
| WO | WO-9210149 A1 | 6/1992 | |
| WO | WO-9312734 A1 | 7/1993 | |
| WO | WO-9624311 A1 | 8/1996 | |
| WO | WO-9736557 A1 | 10/1997 | |
| WO | WO-0230262 A2 | 4/2002 | |
| WO | WO-02096269 A2 | 12/2002 | |
| WO | WO-03092551 A1 | 11/2003 | |
| WO | WO-2006011786 A1 | 2/2006 | |
| WO | WO-2006088359 A1 | 8/2006 | |
| WO | WO-2008131370 A2 | 10/2008 | |
| WO | WO-2009039164 A1 | 3/2009 | |
| WO | WO-2009056836 A2 | 5/2009 | |
| WO | WO-2009056836 A3 | 5/2009 | |

OTHER PUBLICATIONS

"U.S. Appl. No. 12/740,998, Final Office Action mailed Nov. 13, 2012", 12 pgs.

"U.S. Appl. No. 12/740,998, Non Final Office Action mailed May 3, 2012", 7 pgs.

"U.S. Appl. No. 12/740,998, Notice of Allowance mailed Feb. 25, 2013", 5 pgs.

(56) References Cited

OTHER PUBLICATIONS

"U.S. Appl. No. 12/740,998, Preliminary Amendment filed Apr. 30, 2010", 15 pgs.

"U.S. Appl. No. 12/740,998, Preliminary Amendment filed Nov. 23, 2010", 7 pgs.

"U.S. Appl. No. 12/740,998, Response filed Feb. 13, 2013 to Final Office Action mailed Nov. 13, 2012", 11 pgs.

"U.S. Appl. No. 12/740,998, Response filed Aug. 30, 2012 to Non Final Office Action mailed May 3, 2012", 13 pgs.

"U.S. Appl. No. 13/923,768, Notice of Allowance mailed Nov. 26, 2014", 9 pgs.

"U.S. Appl. No. 13/923,768, Response filed Oct. 14, 2014 to Restriction Requirement mailed Aug. 11, 2014", 8 pgs.

"U.S. Appl. No. 13/923,768, Restriction Requirement mailed Aug. 11, 2014", 5 pgs.

"U.S. Appl. No. 13/923,779, Non Final Office Action mailed Jan. 22, 2015", 6 pgs.

"U.S. Appl. No. 13/923,779, Non Final Office Action mailed Jul. 29, 2014", 9 pgs.

"U.S. Appl. No. 13/923,779, Non Final Office Action mailed Sep. 28, 2015", 6 pgs.

"U.S. Appl. No. 13/923,779, Notice of Allowance mailed Mar. 1, 2016", 8 pgs.

"U.S. Appl. No. 13/923,779, Response filed Jun. 22, 2015 to Non Final Office Action mailed Jan. 22, 2015", 9 pgs.

"U.S. Appl. No. 13/923,779, Response filed Nov. 26, 2014 to Non Final Office Action mailed Jul. 29, 2014", 12 pgs.

"U.S. Appl. No. 13/923,779, Response filed Dec. 28, 2015 to Non Final Office Action mailed Sep. 28, 2015", 10 pgs.

"U.S. Appl. No. 14/666,565, Non Final Office Action mailed Jul. 31, 2015", 11 pgs.

"U.S. Appl. No. 14/666,565, Notice of Allowance mailed May 10, 2016", 8 pgs.

"U.S. Appl. No. 14/666,565, Response filed Dec. 28, 2015 to Non Final Office Action mailed Jul. 31, 2015", 8 pgs.

"International Application Serial No. PCT/GB2008/003677, International Preliminary Report on Patentability mailed May 4, 2010", 10 pgs.

"International Application Serial No. PCT/GB2008/003677, Written Opinion mailed Jul. 27, 2009", 9 pgs.

"Japanese Application Serial No. 2013-181571, Office Action mailed Aug. 18, 2014", W/ English Translation, 7 pgs.

"Japanese Application Serial No. 2013-181571, Office Action mailed Aug. 31, 2015", W/ English Translation, 6 pgs.

"Japanese Application Serial No. 2013-181571, Response filed Feb. 18, 2015 to Office Action mailed Aug. 18, 2014", (English Translation of Claims), 6 pgs.

"Japanese Application Serial No. 2013-181571, Response filed Feb. 29, 2016 to Office Action mailed Aug. 31, 2015", (English Translation of Claims), 6 pgs.

"U.S. Appl. No. 14/666,565, Corrected Notice of Allowance mailed Jun. 17, 2016", 4 pgs.

"Japanese Application Serial No. 2013-181571, Examiners Decision of Final Refusal mailed May 30, 2016", W/ English Translation, 5 pgs.

"Japanese Application Serial No. 2013-181571, Response filed Sep. 30, 2016 to Examiners Decision of Final Refusal mailed May 30, 2016", W/Machine Translation, 4 pgs.

\* cited by examiner

PROSTHESIS FOR SIMULATING NATURAL KINEMATICS

CROSS-REFERENCE TO RELATED APPLICATIONS

This application is a continuation of: (1.) U.S. patent application Ser. No. 13/923,768 filed on Jun. 21, 2013, and (2.) U.S. patent application Ser. No. 13/923,779 filed on Jun. 21, 2013, which is a continuation of U.S. patent application Ser. No. 12/740,998 filed Nov. 23, 2010, now U.S. Pat. No. 8,470,048 issued on Jun. 25, 2013, which is a 371 U.S. National Phase Application based on International Application Number PCT/GB2008/003677 filed Oct. 31, 2008, which claims the benefit of: (1.) Great Britain Patent Application No. 0721610.4 filed Nov. 2, 2007, and (2.) Great Britain Patent Application No. 0805917.2 filed Apr. 1, 2008. The entire disclosures of each of the above applications are incorporated herein by reference.

FIELD

The present disclosure relates to a prosthesis for simulating natural kinematics and particularly, but not exclusively, relates to a bearing component and a prosthetic ligament for use in a total knee replacement prosthesis.

BACKGROUND

This section provides background information related to the present disclosure which is not necessarily prior art.

Joint replacement prostheses commonly comprise two bone engaging components that articulate via a bearing component. In a total knee replacement prosthesis, the bone engaging components are a femoral component, comprising an anterior surface with patella track and two femoral condyles, and a tibial component, comprising a substantially planar surface or tray and a post, keel or other stabilizing feature. The femoral and tibial components articulate via a bearing component mounted on the tray of the tibial component. The bearing component may be fully or partially fixed with respect to the tibial component, and commonly comprises a single piece of high density polyethylene.

In order to more closely replicate the natural kinematics of the knee, it is desirable for a total knee replacement prosthesis to facilitate a combination of rolling, rotational and translational movement between the femoral and tibial components of the prosthesis. This can be achieved in part by employing a "mobile" bearing component, having some freedom of movement relative to the tibial component on which it is supported.

SUMMARY

This section provides a general summary of the disclosure, and is not a comprehensive disclosure of its full scope or all of its features.

According to a first aspect, there is provided a bearing component for a joint replacement prosthesis, the component comprising: a first bearing element; a second bearing element, and a linking element, operatively connecting the first and second bearing elements and permitting relative motion there between.

The linking element provides a physical connection between the two bearing elements while still allowing relative motion between the two bearing elements. The linking element thus prevents dislocation of either bearing element in the event of distraction in either compartment of the prosthesis in which the bearing element is employed.

The linking element may be flexible and may be elastic or resilient. Such a linking element thus affords a greater range of relative motion between the two bearing elements The first and second bearing elements and the linking element may be integrally formed. The linking element may comprise a polyethylene membrane.

Alternatively, the linking element may comprise a fabric or polyester cord.

Respective ends of the linking element may be molded into the first and second bearing elements. The linking element may extend into and through bores that may extend at least partially through the bearing elements.

According to another aspect, there is provided a joint replacement prosthesis comprising first and second bone engaging components that articulate via the bearing component.

The prosthesis may be a knee replacement prosthesis, the first bone engaging component comprising a femoral component and the second bone engaging component comprising a tibial component.

The bearing component may be supported on the tibial component such that relative motion between the tibial component and first and second bearing elements is enabled.

The articulation between the femoral component and the first and second bearing elements may be at least partially spherical.

The tibial component may comprise at least one tray, on which the bearing component is supported, and a retaining element that extends across the tray, between the first and second bearing elements, passing over the linking element. The retaining element may thus prevent dislocation of the entire bearing component in the event of bilateral distraction.

The retaining element may comprise a bridge, under which the linking element of the bearing component passes, such that the bridge limits the extent of relative motion possible between the linking element and the tibial tray.

The retaining element may be removably connected to the tibial tray, thus facilitating assembly of the prosthesis.

The joint replacement prosthesis may further comprise an artificial ligament.

The artificial ligament may extend between and be connected to the tibial and femoral components. The artificial ligament may engage the retaining element during at least part of its range of movement. The retaining element may be adapted to support and/or deflect the artificial ligament and/or to change a line of action of the ligament. For example, the retaining element may comprise a pulley or have a ligament support surface which has a recess or is waisted to align the ligament and to prevent dislocation. The ligament support surface may be curved and/or chamfered and/or polished to reduce wear of the artificial ligament.

The tibial component of the joint replacement prosthesis may comprise first and second bearing surfaces, operable to articulate with the first and second bearing elements of the bearing component, the first bearing surface being convex and the second bearing surface being non con-convex.

The second bearing surface may be concave. The convex and concave bearing surfaces may be at least partially spherical.

According to another aspect, there is provided a method of making a bearing component of the present invention comprising direct compression moulding ends of the linking element into the first and second bearing elements.

According to another aspect, there is provided a method of making a bearing component comprising moulding the first and second bearing elements as a single piece and removing material from the area between the first and second bearing components to define the linking element.

According to another aspect, there is provided a flexible linking element for use in preventing dislocation of mobile bearings in a total knee replacement prosthesis.

The flexible linking element may connect first and second mobile bearing elements. Movement of the flexible linking element may be at least partially constrained by a retaining element.

According to another aspect, there is disclosed use of a flexible linking element to prevent dislocation of mobile bearings in a total knee replacement prosthesis.

The flexible linking element may connect first and second mobile bearing elements. Movement of the flexible linking element may be at least partially constrained by a retaining element.

According to another aspect, there is provided a tibial component for a knee replacement prosthesis, the component comprising a lateral compartment having a convex bearing surface and a medial compartment having a non-convex bearing surface. The convex lateral bearing surface provides increased stability to the lateral compartment of the joint, when the tibial component is assembled in a knee replacement prosthesis.

The bearing surface of the medial compartment may be concave. Such a concave medial compartment provides greater stability and facilitates in replicating the natural motion of the knee when the tibial component is assembled in a knee replacement prosthesis, primarily by reducing motion in the medial compartment of the knee. Combining a convex lateral compartment with a concave medial compartment facilitates restoration of the natural motion of the knee.

Alternatively, the bearing surface of the medial compartment may be planar.

The lateral and medial bearing surfaces may be part spherical and the radii of curvature of the lateral and medial bearing surfaces may be substantially the same. The centre of curvature of each bearing surface may be anterior of the anterior/posterior centre line of the bearing surface and on the medial/lateral centre line of the bearing surface.

The lateral and/or medial bearing surfaces may comprise modular surface components, operable to be connected to a tray component to form the tibial component. The modular surface components and tray component may comprise cooperating fittings to facilitate connection and removal of the modular surface components.

According to another aspect, there is provided a kit of parts for a tibial component of a knee prosthesis, the kit comprising a tibial tray and a plurality of surface components, operable to be removably connected to the tray, the surface components each comprising a bearing surface, at least one surface component comprising a convex bearing surface and at least one surface component comprising a concave bearing surface.

According to another aspect, there is provided a knee replacement prosthesis comprising the bearing component and the tibial component.

It is known to implant an artificial ligament to replace a natural ligament which has become damaged. Conventional artificial ligaments are formed from strands or bundles of artificial fibres which may be woven and/or aligned to form a flexible member which is substantially uniform in size and is resilient along its length.

A natural ligament exhibits high strength, toughness and resilience and retains these properties for many years. To date, it has been impossible to match these properties using artificial fibres.

When implanted, artificial ligaments may be attached to existing bone tissue, provided the tissue at the attachment site is relatively intact. However, if surrounding bone tissue is diseased or damaged, it may be necessary to remove both the natural ligament and the adjacent bone tissue and replace them with prosthetic components.

Joint replacement operations commonly result in removal of at least one ligament. The functionality of the ligament is replicated as closely as possible by one or more features of the replacement prosthesis (as for example in the case of a cooperating cam and post in a total knee replacement). However, it has proved extremely difficult to replicate the natural kinematics of a joint without the presence of naturally functioning ligaments. This is particularly evident in the case of the knee joint, which exhibits a complex movement that is highly dependent upon the interaction of ligaments with the articulating areas of bone.

According to another aspect, there is provided a joint replacement prosthesis comprising an artificial ligament, which is adapted to replace a human or animal ligament, and a biasing element operatively coupled to the artificial ligament to control the effective stiffness of the artificial ligament.

The biasing element may have a stiffness approximating that of a natural ligament that is to be replaced. In this manner, the biasing element may assist in replicating the natural characteristics of the joint. The biasing element may have linear or non-linear stiffness characteristics which may be achieved by methods known in the art. The stiffness of the biasing element may be in a range of 3 N/mm to 40 N/mm.

The biasing element may comprise one or more springs and/or one or more elastic or elastomeric members and/or one or more Belleville washers. The biasing element may comprise a cylinder, tube, toroid, cone or loop of elastic or elastomeric material.

The biasing element may be a coil spring and may be a tension spring or a compression spring. Alternatively the biasing element may be a leaf spring. The leaf spring may engage an abutment at a predetermined position in its range of movement to vary the effective stiffness of the spring.

The spring may be conical, so that it provides variable stiffness over its range of movement. It may, for example, be a conical coil spring.

The biasing element may be operatively coupled to the ligament at or near one end only of the ligament. The biasing element may engage the ligament via a bearing component.

According to another aspect, there is provided a joint replacement prosthesis comprising an artificial ligament, which is adapted to replace a human or animal ligament, and a tensioning element operatively coupled to the ligament for applying tension to the ligament.

The tensioning element may be operatively coupled to the ligament at or near one end only of the ligament.

The prosthesis may further comprise a biasing element, which may comprise an elastic element. The biasing element may act between the tensioning element and the ligament. The tensioning element may be coupled to the ligament via the biasing element. The biasing element may engage the ligament via a bearing element.

The biasing element may be formed as in the previous aspect. For example, it may comprise a spring, which may be a compression spring. The spring may be of any form. For example it may comprise a coil spring, a leaf spring, a Belleville washer or an elastic or elastomeric member.

The biasing element may have a stiffness approximating that of a natural ligament that is to be replaced. The biasing element may have a linear stiffness characteristic. Alternatively, the biasing element may have a non-linear stiffness characteristic.

The ligament may be coupled to the tensioning element via an attachment means. The attachment means may comprise an enlarged portion that is formed on the ligament and engages the tensioning element. For example, the enlarged portion may comprise a knot tied in the artificial ligament.

The prosthesis may further comprise a bone engaging element for attachment to a bone. The tensioning element may act between the bone engaging element and the artificial ligament.

The tensioning element may be at least partially housed within the bone engaging element. The bone engaging element may comprise a stem, and the tensioning element may be at least partially housed within the stem.

The tensioning element may be adjustable and may be operable to adjust the tension within the ligament. The adjustable tensioning element therefore enables the tension in the ligament to be adjusted in a controlled manner, independently and controllably altering the characteristics of the ligament.

The prosthesis may further comprise adjustment means operable to adjust the tension in the ligament. The tension may be adjusted by adjusting the position of the tensioning element relative to the bone engaging element. Thus tension in the ligament may be altered even after both ligament and bone engaging element have been implanted into a patient.

The adjustment means may comprise a threaded connection between the tensioning element and the bone engaging element. The tensioning element may comprise an external thread and the stem may comprise a corresponding internally threaded bore within which the tensioning element is received.

The tensioning element may be configured to be screwed into or out of the bore to adjust the tension in the ligament.

The tensioning element may be accessed through an opening formed in the bone engaging element.

The prosthesis may further comprise a retaining element for limiting the motion of one or more bearing elements of the prosthesis, the retaining element being adapted to engage an artificial ligament to thereby change a line of action of the ligament.

The prosthesis may comprise only part of a joint replacement prosthesis, which may be a knee replacement prosthesis.

The prosthesis may comprise at least part of a knee replacement prosthesis in which the bone engaging element comprises a tibial component and the artificial ligament comprises a replacement anterior cruciate ligament (ACL).

Artificial ligaments without suitable stiffness characteristics do not balance with the other soft tissue, resulting in abnormal kinematics. By using a ligament with physiological stiffness, there will be mutual respect with the retained soft tissue, allowing the joint to function normally.

The biasing element and/or tensioning element can protect the ligament from excess load. It has been shown that the loads induced in an artificial ligament which is substantially inextensible are far in excess of the ultimate tensile stress of a natural ligament. By allowing just a small amount of extension in the artificial ligament, these loads are reduced and the ligament and its attachment are protected.

The biasing element and/or tensioning element can enable the tension of the ligament to be balanced with other soft tissues. This eases the implantation of an artificial ligament because fixation can be optimised first before applying tension to a ligament. In embodiments with an adjustable tensioning element and/or with adjustable fixation of the ligament to the femur a single size or limited range of sizes of artificial ligament can be used on any patient. This reduces the inventory requirements for artificial ligaments.

According to another aspect, there is provided a joint replacement prosthesis comprising a bone engaging element having a stem which is adapted to project into a bone, and an artificial ligament, an end of the ligament extending into and being secured within the stem.

The prosthesis may comprise at least part of a joint replacement prosthesis, which may be a knee replacement prosthesis.

The prosthesis may comprise at least part of a knee replacement prosthesis in which the bone engaging element comprises a tibial component and the artificial ligament comprises a replacement anterior cruciate ligament (ACL).

The ligament may be secured within the stem of the bone engaging element via a tensioning element, the tensioning element being at least partially housed within the bone engaging element.

The ligament may be secured within the stem of the bone engaging element via a biasing element, the biasing element being at least partially housed within the bone engaging element.

The ligament may be secured within the stem of the bone engaging element via both a tensioning element and a biasing element, the tensioning element and the biasing element being at least partially housed within the bone engaging element.

According to another aspect, there is provided a prosthesis comprising a bone engaging element and an artificial ligament, an end of the artificial ligament being secured to the body of the bone engaging element, the prosthesis further comprising a ligament support, the ligament support at least partially determining the line of action of the ligament.

The artificial ligament may be secured within a recess formed in the body of the bone engaging element, and the ligament support may comprise a mouth of the recess. The mouth of the recess may be radiused or chamfered.

The ligament support may be shaped like a pulley. For example it may be substantially cotton reel shaped or otherwise formed with a recess or waisted portion. This recess or waisted portion is helpful in centring the artificial ligament and reduces the possibility of dislocation.

The ligament support may project from a surface of the bone engaging element, or may be formed on the retaining element described in previous aspects. Alternatively, the artificial ligament may be secured to the bone engaging element or to the retaining element.

The prosthesis may comprise at least part of a knee replacement prosthesis.

This aspect allows the direction of action of an artificial ligament to be changed, in particular where a biasing element is used to control the stiffness of the assembly. For example, if the biasing element is housed within the tibial stem of a knee replacement prosthesis its line of action must be parallel to that stem. However, the line of action of the ligament must be towards a point of attachment to the femoral component or femur, the position of which changes through the range of motion. The use of a ligament support allows for the necessary change in the direction of the line of action of the ligament.

According to another aspect, there is provided a method of implanting a prosthesis comprising first and second bone engaging elements, an artificial ligament and a biasing element, comprising: (a) operatively coupling the biasing element to a first end of the artificial ligament; (b) operatively coupling the biasing element to the first bone engaging element; (c) implanting the first and second bone engaging elements into bone tissue; (d) connecting a second end of the artificial ligament to the second bone engaging element, (e) balancing tension within the artificial ligament.

According to another aspect, there is provided a method of implanting a prosthesis comprising first and second bone engaging elements, an artificial ligament and an adjustable tensioning element operatively coupled to a first end of the artificial ligament and to the first bone engaging element, the method comprising: (a) assembling the first bone engaging element, adjustable tensioning element and artificial ligament; (b) implanting the first and second bone engaging elements into bone tissue; (c) connecting a second end of the artificial ligament to the second bone engaging element; (d) adjusting the position of the adjustable tensioning element until a predetermined tension within the artificial ligament is achieved.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
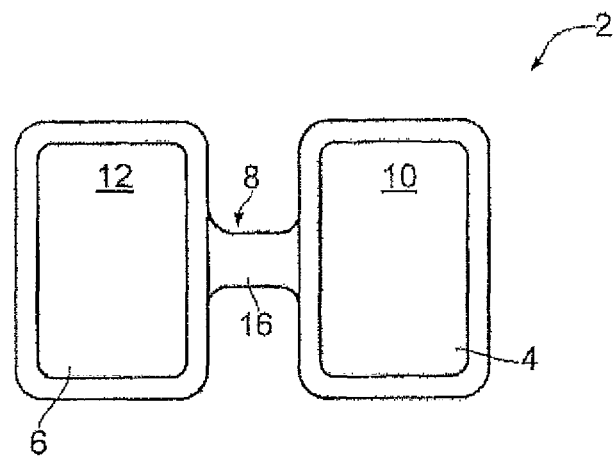
Figure 3:
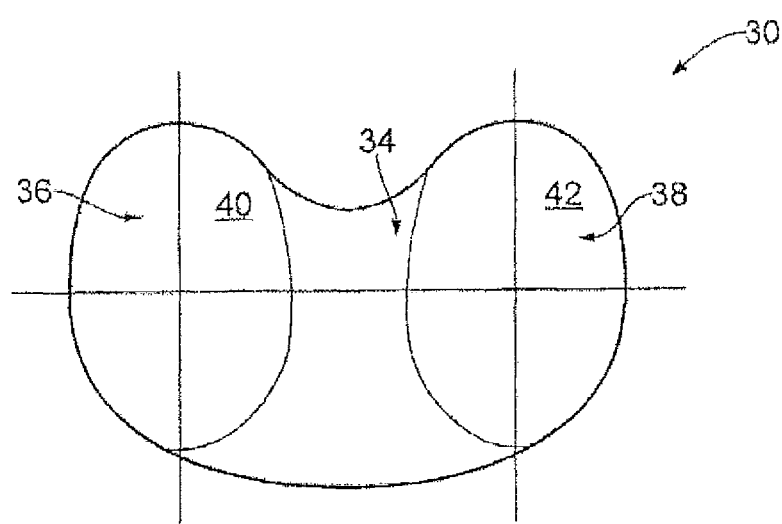
Figure 4:
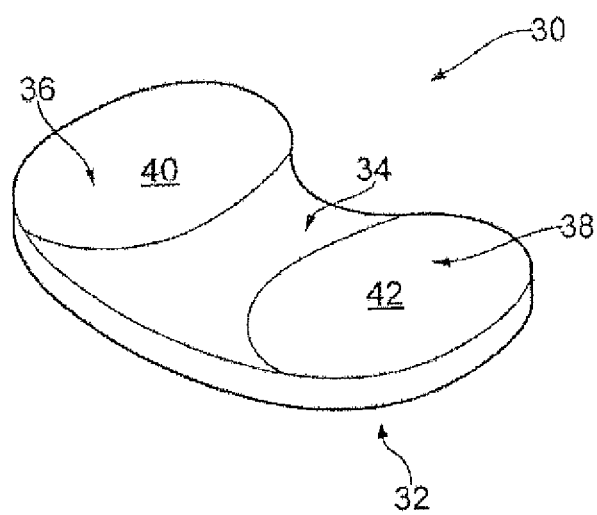
Figure 5:
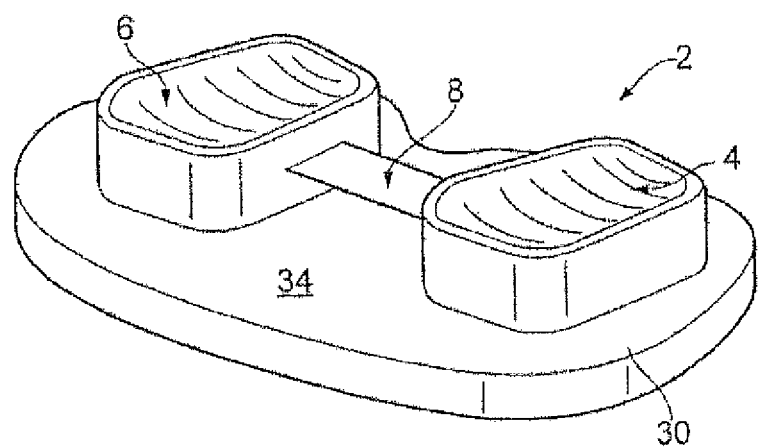
Figure 6:
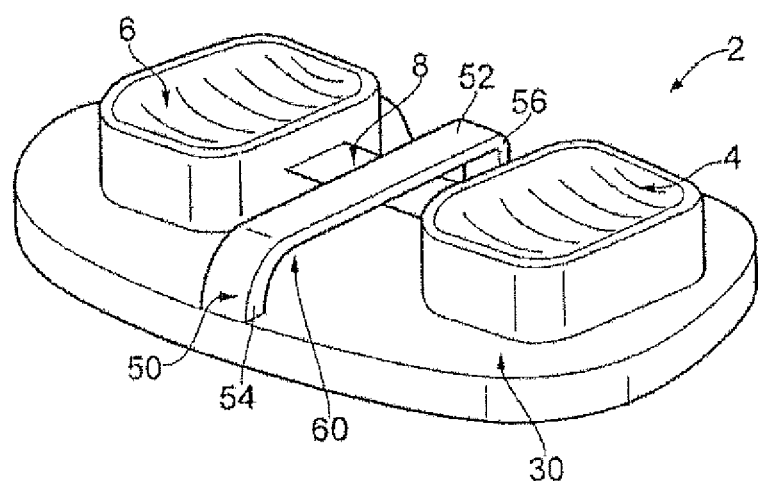
Figure 7:
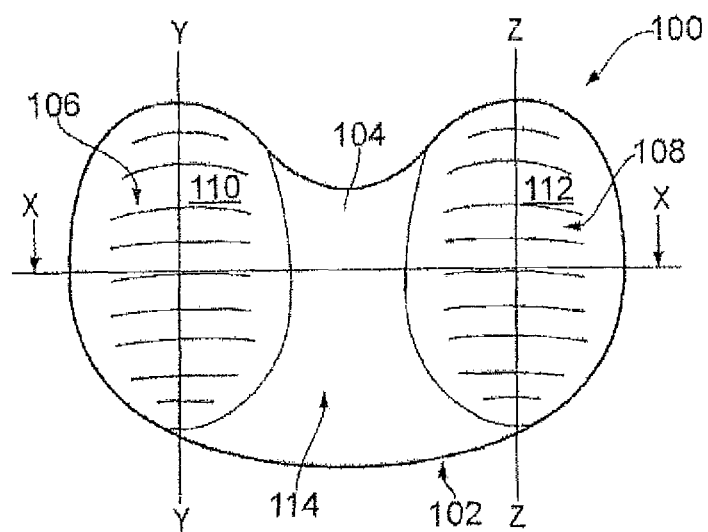
Figure 8:
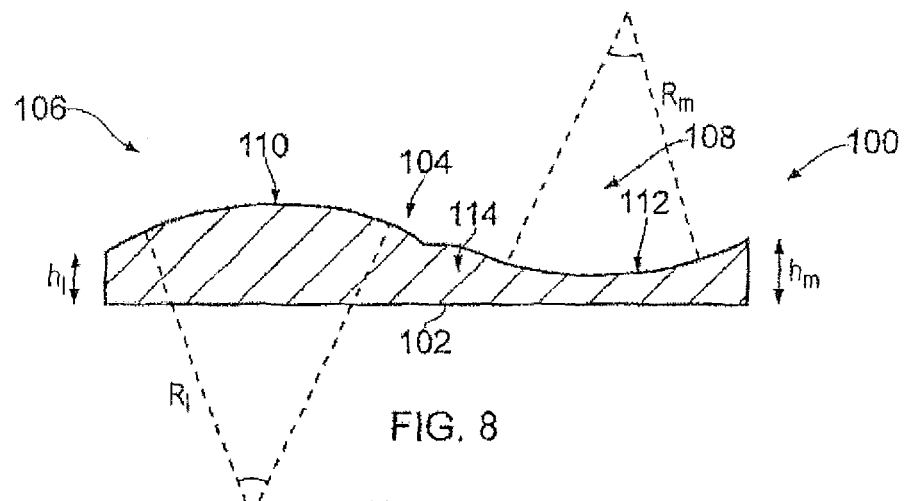
Figure 9:
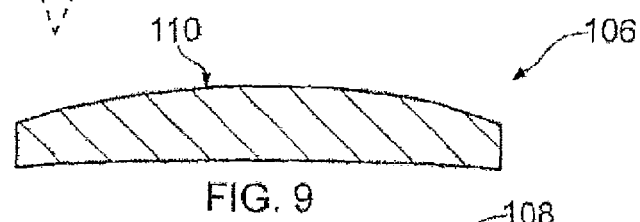
Figure 10:
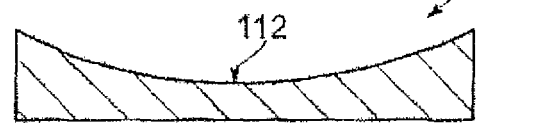
Figure 12:
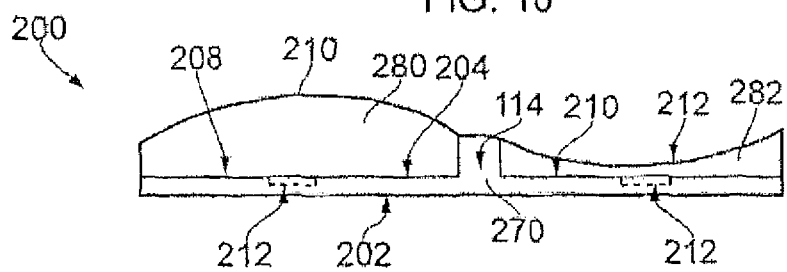
Figure 13:
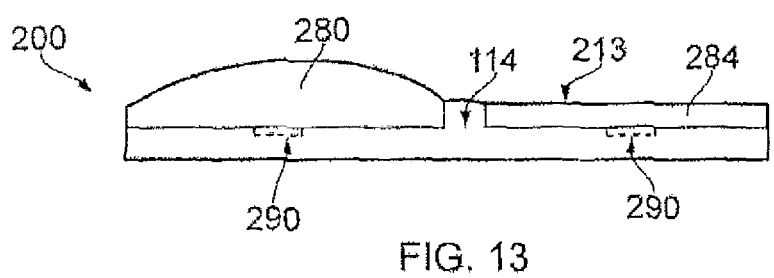
Figure 11:
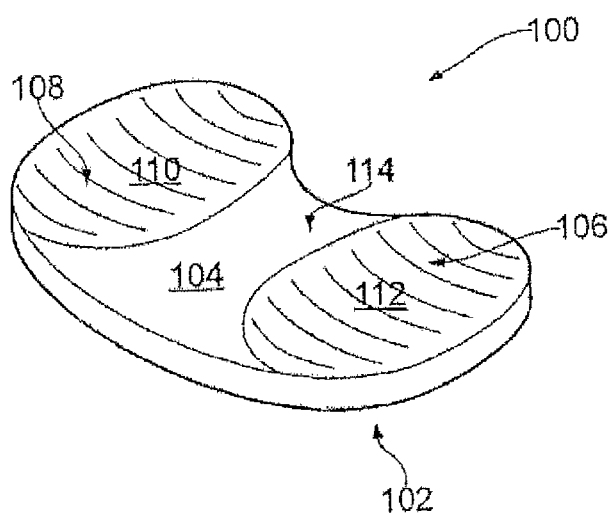
Figure 14:
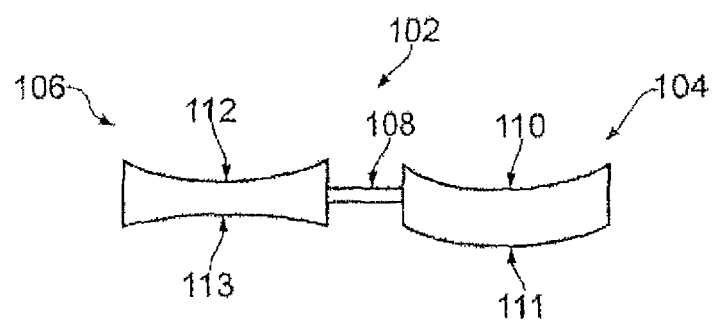
Figure 15:
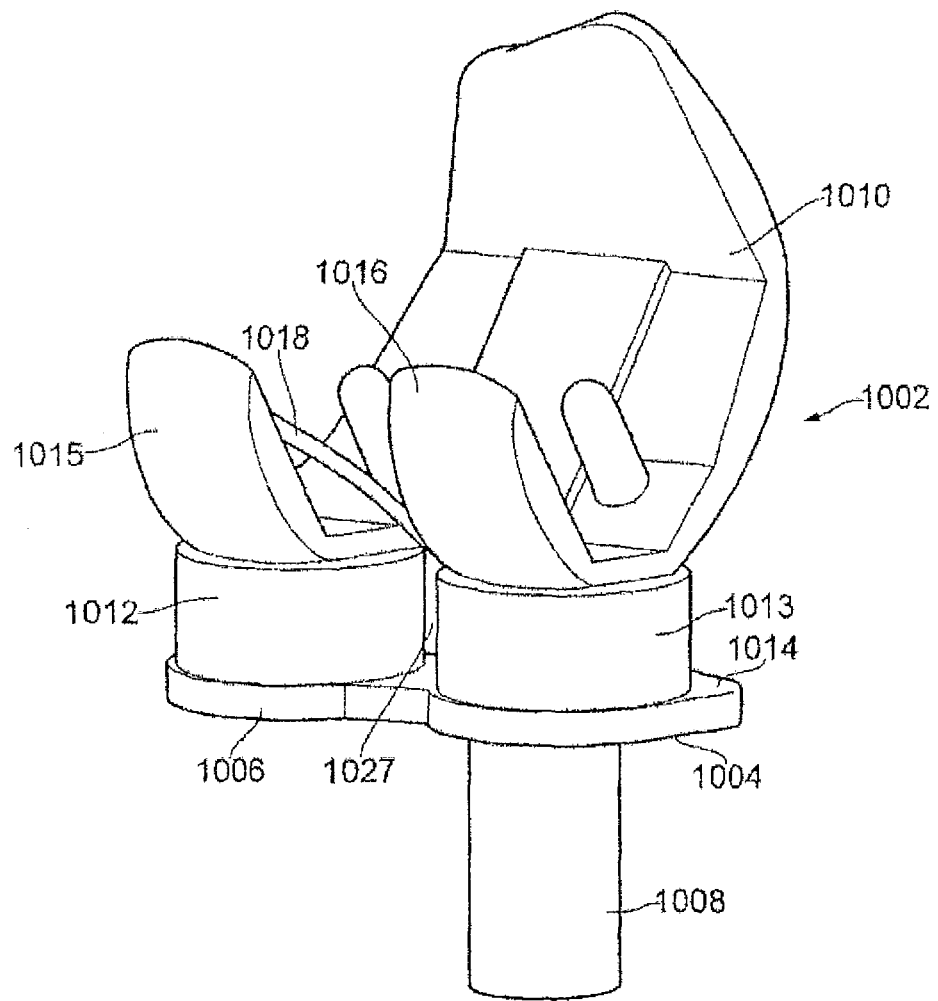
Figure 16:
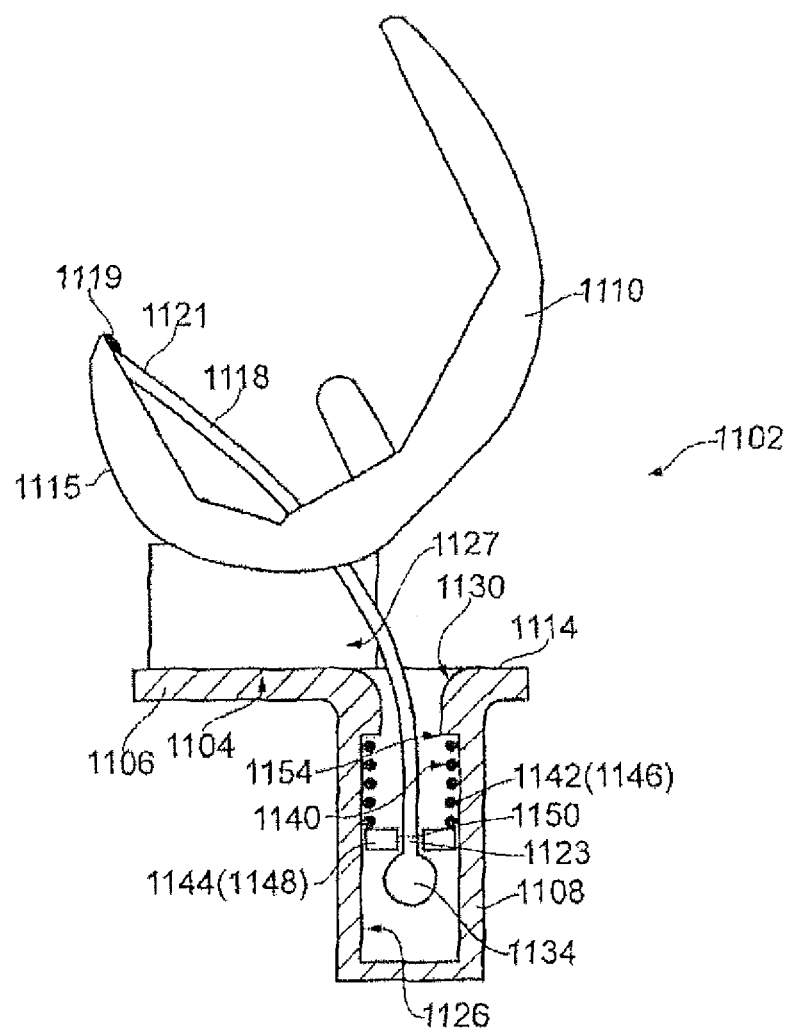
Figure 17:
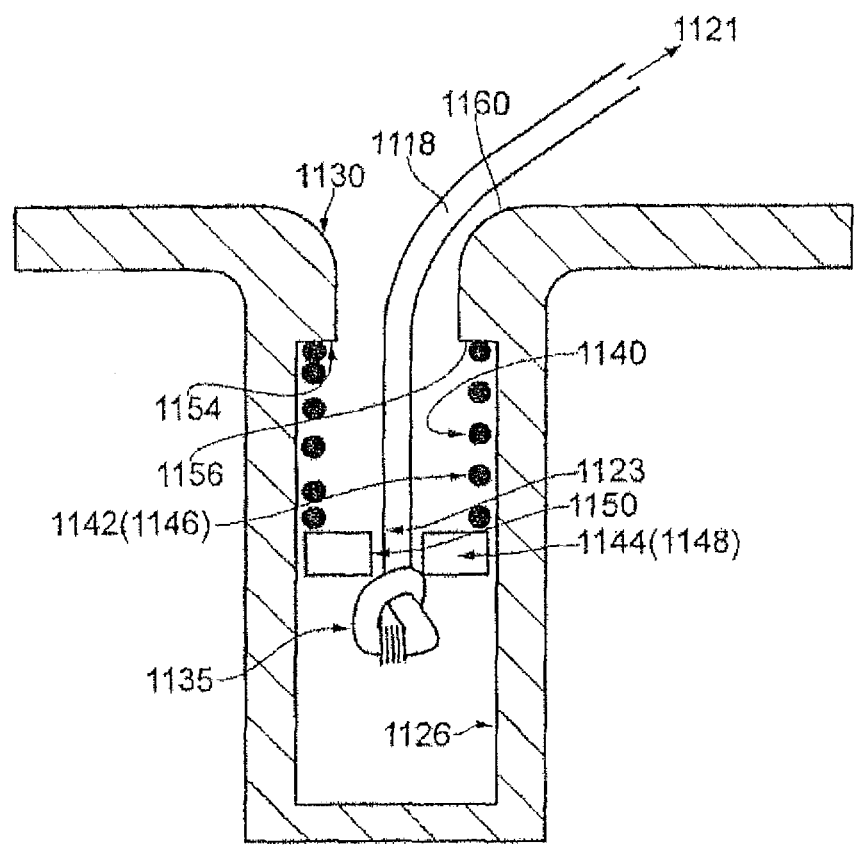
Figure 18:
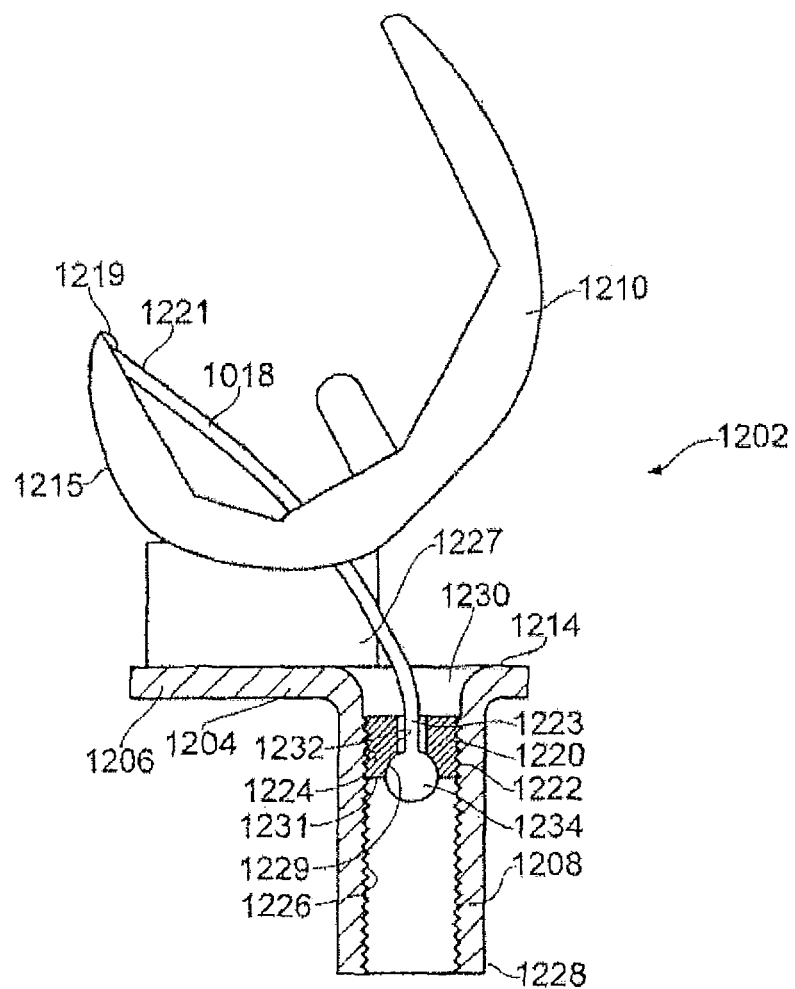
Figure 19:
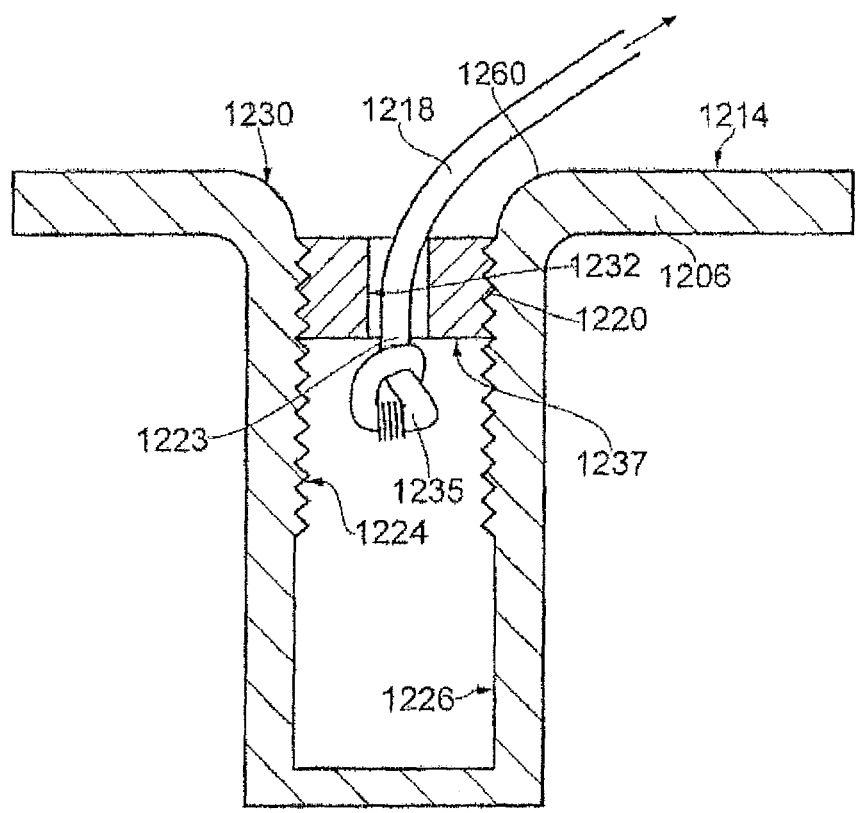
Figure 20:
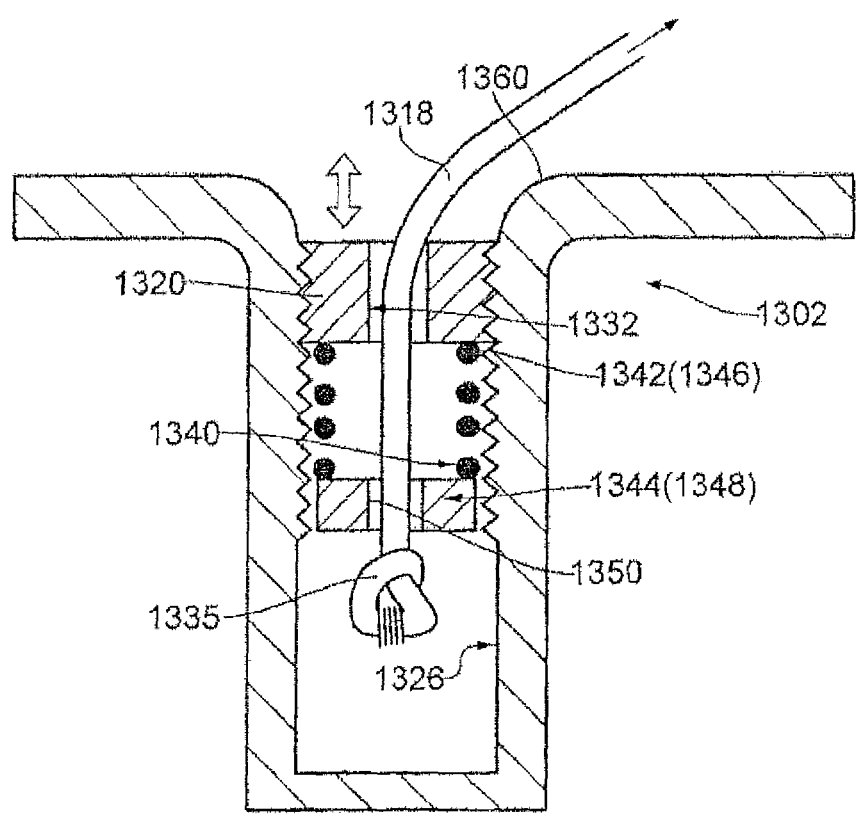
Figure 21:
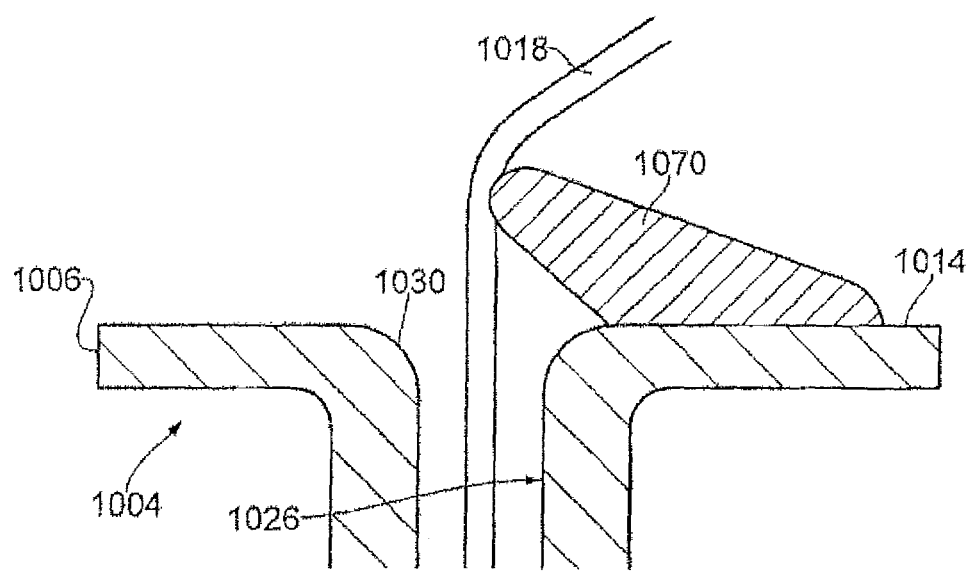
Figure 22:
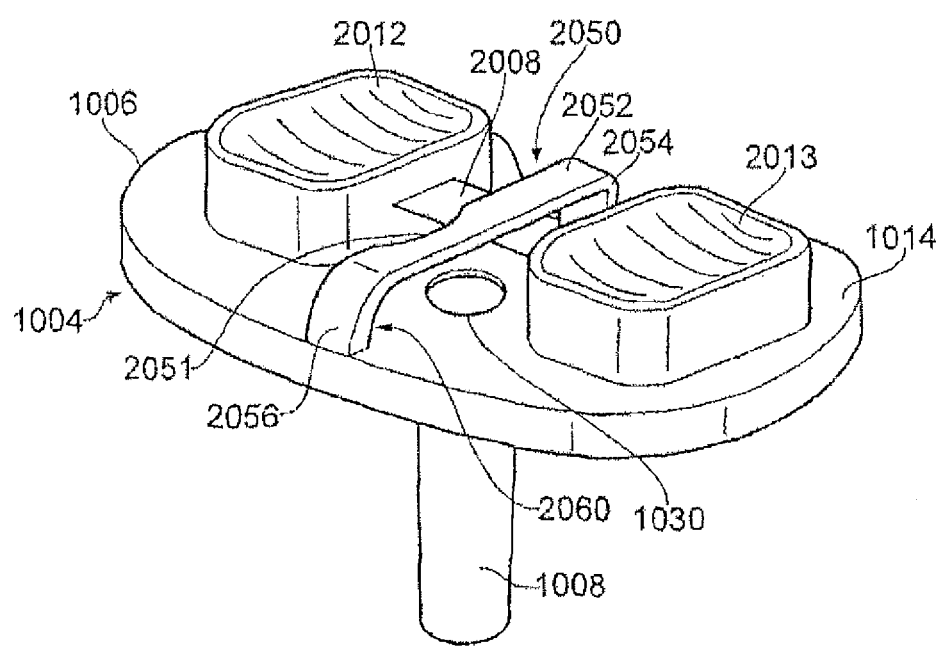

FIG. 1 is a plan view of a bearing component
FIG. 2 is a plan view of an alternative bearing component
FIG. 3 is a plan view of a tibial tray component
FIG. 4 is a perspective view of the tibial tray component of FIG. 3
FIG. 5 is a perspective view of the bearing component and the tibial tray component
FIG. 6 is a perspective view of a partially assembled knee replacement prosthesis
FIG. 7 is a plan view of an embodiment of a tibial component
FIG. 8 is a sectional view along the anterior/posterior centre line XX of the component of FIG. 7.
FIG. 9 is a sectional view along the medial/lateral centre line YY of the lateral compartment of the component of FIG. 7.
FIG. 10 is a sectional view along the medial/lateral centre line ZZ of the medial compartment of the component of FIG. 7.
FIG. 11 is a perspective view of an embodiment of a tibial component
FIG. 12 is a sectional view of another embodiment of a tibial component
FIG. 13 is a sectional view of the component of FIG. 12 in an alternative arrangement
FIG. 14 is a sectional view of an embodiment of a bearing component
FIG. 15 is a perspective view of a knee prosthesis having an artificial ligament.
FIG. 16 is a partially sectioned side view of a knee prosthesis having an artificial ligament secured via a biasing element.
FIG. 17 is a partial sectional view of the embodiment of FIG. 16.
FIG. 18 is a partially sectioned side view of a knee prosthesis having an artificial ligament secured via a tensioning device.
FIG. 19 is a partial sectional view of the embodiment of FIG. 18.
FIG. 20 is a partial sectional view of a knee prosthesis having an artificial ligament secured via a tensioning device and a biasing device.
FIG. 21 is a partial sectional view of a knee prosthesis having an artificial ligament and a ligament support.
FIG. 22 is a perspective view of a partially assembled knee replacement prosthesis with a modified ligament support. Corresponding reference numerals indicate corresponding parts throughout the several views of the drawings.

DETAILED DESCRIPTION

Example embodiments will now be described more fully with reference to the accompanying drawings.

With reference to FIGS. 1 and 2, a bearing component 2 comprises first and second bearing elements 4, 6 and a flexible linking element 8. Bearing component 2 is suitable for use as a meniscal bearing component of a total knee prosthesis, the prosthesis comprising a tibial component, a femoral component and the bearing component 2. Bearing elements 4, 6 of the bearing component are formed of moulded high density polyethylene and each comprise a distal bearing surface (not shown), that is shaped to articulate with a tibial tray, and a proximal bearing surface 10, 12, that is shaped to articulate with an associated condyle of a femoral prosthesis. The proximal bearing surfaces 10, 12 may have any suitable shape appropriate for the chosen femoral component with which the bearing component is to articulate.

The linking element 8 may be a separate cord 14, connected to the bearing elements 4, 6, as illustrated in FIG. 1. The cord 14 may be of any appropriate shape or material. For example, it may comprise a woven flexible fabric or polyester cord. The cord 14 passes through appropriately dimensioned bores 18, 20 that extend across the width of the bearing elements 4, 6 such that ends of the cord 14 extend out of opposite sides of each bearing element 4, 6. A knot 22 is tied in each end of the cord 14 to prevent the cord 14 passing back through the bores 18, 20. The two bearing elements 4, 6 are thus connected together. Relative movement between the bearing elements 4, 6 is possible, as the cord 14 is flexible. In alternative embodiments, the knot 22 may be replaced by a ball or other protruding feature that prevents passage of the ends of the cord back through the bores 18, 20. In another embodiment, as illustrated for example in FIGS. 5 and 6, the cord 14 may be moulded into the bearing elements at the time of manufacture.

In an alternative embodiment, the linking element 8 may be an integral component 16 of the bearing elements 4, 6, as illustrated in FIG. 2. The linking element may for example comprise a thin polyethylene membrane 16 that connects the bearing elements 4, 6 while permitting relative motion there between. The membrane 16 may be moulded into the bearing elements 4, 6 or may be formed during manufacture of the bearing elements by forming the bearing component 2 as a single component and then removing material from the component so as to define the two bearing elements 4, 6, leaving only the thin membrane of material 16 connecting the two elements together.

With reference to FIGS. 3 to 6, a tibial component suitable for use with the bearing component 2 comprises a tray 30 and a bridge element 50. The bridge element 50 is omitted in FIGS. 3 to 5 for clarity. The tray 30 is formed of a suitable biocompatible metal, such as stainless steel or cobalt chromium molybdenum. The tray comprises a distal surface 32, which engages a resected tibial bone surface, and may comprise a keel or other stabilising feature (not shown). The tray 30 further comprises a proximal surface 34 that articulates with the distal surfaces of the bearing elements 4, 6 of the bearing component 2, when the bearing component 2 and tibial component are assembled. The tibial component comprises a lateral compartment 36 and a medial compartment 38. The lateral and medial compartments may each comprise bearing surfaces 40, 42 with which the bearing elements 4, 6 of the bearing component 2 articulate. The bearing surfaces 40, 42 may be planar, and the articulation may comprise sliding articulation.

With reference particularly to FIG. 6, the bridge element 50 comprises a beam 52 and two supporting legs 54, 56. The beam 52 extends substantially parallel to the proximal surface 34 of the tibial tray 30 in an anterior/posterior direction and spans substantially the entire width of the tray 30. The supporting legs 54, 56 are positioned proximate the anterior and posterior edges of the tray, substantially equidistant of the medial and lateral edges of the tray 30. The bridge element 50 thus divides the tray 30 into its lateral and medial compartments 36, 38 and defines a passage 60 there between. A proximal surface of the beam 52 may comprise a threaded blind bore and cooperating screw (not shown), suitable for attaching one end of an artificial ligament (not shown) to the bridge element 50. Alternative means of connecting an artificial ligament may also be used.

The bridge element 50 is formed of any suitable biocompatible metal and may be formed integrally with the tibial tray 30. Alternatively, the bridge element may be connected to the tray 30 in any appropriate manner. Preferably, the bridge element 50 is removably connected to the tray 30, facilitating assembly of the final prosthesis. Alternatively, the bridge element 50 may be fixedly connected to the tray 30 at the time of manufacture.

The bearing component 2 and tibial tray 30 may be assembled at the time of manufacture or immediately prior to implantation. When the bearing component 2 and tibial tray 30 are assembled, as illustrated in FIG. 5, the bearing elements 4, 6 of the bearing component 2 each rest on a respective bearing surface 40, 42 of the tray 30. The linking element 8 of the bearing component 2 connects the bearing elements 4, 6 together. When the bridge element 50 is assembled with the tray 30 to form the tibial component, as illustrated in FIG. 6, the linking element 8 of the bearing component extends under the beam 52 of the bridge element, through the passage 60 to connect the bearing element 4, 6. If the bridge element 50 is integrally formed with the tibial tray 30, the tray 30, bridge element 50 and bearing component 2 may be assembled at the time of manufacture. Alternatively, if the bridge element 50 is not integrally formed with the tray 30 but may be connected to the tray after manufacture, then the tray 30, bridge element 50 and bearing component 2 may be assembled at any time prior to implantation.

In use, the tibial tray 30, bridge element 50 and bearing component 2 are assembled and implanted by mounting the tibial component onto a resected proximal surface of a tibia.

A femoral component is attached to a distal surface of a femur and the resurfaced joint is assembled. The bearing elements 4, 6 cushion the articulation between the tibial tray and the condyles of the femoral component. The bearing elements 4, 6 are mobile but are retained safely within the joint by the combined action of the linking element 8 and the bridge element 52. In the event of distraction of the joint in either the lateral or medial compartments, the bearing element in the distracted compartment is held within the joint by its connection to the other bearing element via the linking element 8. In the event of bilateral distraction, the bearing component 2 is held within the joint space by the bridge 52. The passage 60 defined by the bridge element 50 is not sufficiently large to allow passage of either of the bearing elements 4, 6, so dislocation of the bearing component 2 is prevented.

With reference to FIGS. 7 to 11, a tibial component 100 of a knee prosthesis comprises a distal surface 102, that is operable to engage a resected surface of a tibia, and a proximal surface 104, that is operable to engage one or more bearing components (not shown). The component may further comprise a post, keel or other stabilising feature (not shown) that extends from the distal surface and provides stability to the component 100 when implanted. The component comprises a lateral compartment 106, including a lateral portion of the proximal and distal surfaces 102, 104, and a medial compartment 108, including a medial portion of the proximal and distal surfaces 102, 104. The lateral and medial compartments are separated by a central region 114.

Each of the lateral and medial compartments comprises a proximal bearing surface 110, 112. The lateral proximal bearing surface 110 is convex or domed, having a part spherical surface with a radius of curvature $R_l$. The centre of curvature of the lateral bearing surface 110 is just anterior of the anterior/posterior centre line XX of the tibial component 100, and is approximately on the medial/lateral centreline YY of the lateral compartment 106 of the tibial component 100. The medial proximal bearing surface 112 is concave or dished, having a part spherical surface with a radius of curvature $R_m$, which is preferably of a similar length to the lateral bearing surface radius of curvature $R_l$. The centre of curvature of the medial bearing surface 112 is also just anterior of the anterior/posterior centre line XX of the tibial component 100, and is approximately on the medial/lateral centreline ZZ of the medial compartment 108 of the tibial component 100.

Kinematic analysis of a patient may be employed to determine the height $h_m$, $h_l$ of each compartment of the tibial component 100. Alternatively, the heights $h_l$, $h_m$ of the lateral and medial compartments may be selected according to the natural positions of the lateral and medial bearing surfaces of the healthy tibia.

With reference to FIGS. 12 and 13, another embodiment of tibial component 200 comprises a tibial tray 270 and at least three modular surface components 280, 282, 284. The tibial tray 270 comprises a distal surface 202, that is operable to engage a resected surface of a tibia, and a proximal surface 204, that is operable to engage one or more modular surface components. The proximal surface 204 comprises lateral and medial support surfaces 208, 210, each of which may comprise a connection feature, for example a recess 212, operable to cooperate with a corresponding connection feature on a corresponding modular surface component, as described below.

The at least three modular surface components comprise a domed lateral surface component 280, having a convex part spherical proximal bearing surface 210 as described above with respect to tibial component 100, a dished medial surface component 282, having a concave part spherical proximal bearing surface 212 as described above with respect to tibial component 100, and a planar medial surface component 284, having a planar proximal bearing surface 213. The tibial component 200 may also comprise a lateral planar surface component having a planar proximal bearing surface (not shown). Each modular surface component 280, 282, 284 comprises a distal bearing surface that articulates with a corresponding support surface 208, 210 of the tibial tray 270. The distal bearing surfaces of the modular surface components 280, 282, 284 each comprise a connection feature, for example a lug 290, operable to cooperate with the corresponding connection feature on the corresponding tibial support surface 208, 210.

The tibial component 200 may be provided as a kit of parts comprising a tibial tray 270 and a selection of modular surface components 280, 282, 284, enabling a surgeon to select an appropriate combination of domed, dished and planar bearing surfaces to suit a particular patient.

Both embodiments of tibial component 100, 200 are operable to be used in combination with appropriately shaped bearings (not shown). The bearings comprise individual medial and lateral bearings, each having a proximal femoral bearing surface that is shaped to articulate with a femoral component of a knee prosthesis, and a distal tibial bearing surface that is shaped to articulate with the appropriate one of the lateral or medial bearing surfaces of the tibial component 100, 200. A combination of domed lateral and dished medial bearing surfaces on the tibial component 100, 200 provides increased stability to individual meniscal bearings, and facilitates in recreating the natural motion of the knee.

The tibial components 100, 200 described with reference to FIGS. 7 to 13, may used in combination with the bearing component 2 described with reference to FIGS. 1 to 6. A bridge element 50 as described above with respect to FIG. 6 may be mounted in the central region 114 of the tibial component 100, 200 of FIGS. 7 to 13. If the bearing component 2 is to be used in connection with a tibial component 100, 200 as described with reference to FIGS. 7 to 13, the distal bearing surfaces of the bearing elements 4, 6 of the bearing component 2 are shaped to articulate with, for example, the convex and concave bearing surfaces 210, 212 of the tibial component 200. An example of a bearing component 102 for use with either of the tibial components 100, 200 of FIGS. 7 to 13 is illustrated in sectional view in FIG. 14. The bearing component 102 comprises lateral and medial bearing elements 106, 104, each of which comprises a proximal bearing surface 110, 112, shaped to articulate with an associated femoral condyle. The bearing elements 104, 106 further comprise distal bearing surfaces 113, 111, each of which is shaped to articulate with a corresponding proximal tibial bearing surface 210, 212. Thus, the distal bearing surface 113 of the lateral bearing element 106 is part spherical concave, having a radius of curvature substantially equal to the radius of curvature $R_l$ of the lateral bearing surface 210 of the tibial component. Similarly, the distal bearing surface 111 of the medial bearing element 104 is part spherical convex, having a radius of curvature substantially equal to the radius of curvature $R_m$ of the medial bearing surface 212 of the tibial component.

It will be understood by one skilled in the art that any aspect of any of the embodiments described herein may be used in combination with any other aspect of any of the embodiments described herein.

Referring to FIG. 15, a knee prosthesis 1002 comprises a tibial component 1004 having a tibial tray 1006 integrally formed with a stem 1008, a femoral component 1010 and a pair of bearing components 1012, 1013. The bearing components 1012, 1013 separate the tibial component 1004 and femoral component 1010, and are formed with proximal and distal bearing surfaces which engage corresponding bearing surfaces 1014, 1015, 1016 on the tibial tray 1006 and on the femoral component 1010. These various bearing surfaces enable the tibial component 1004 to rotate and translate relative to the femoral component 1010. The bearing components 1012, 1013 may be meniscal bearing components, rotational platform bearing components, or fixed bearing components and may be joined bearing components which may be shaped and may articulate in accordance with the embodiments of FIGS. 1 to 14.

FIGS. 16 and 17 illustrate an embodiment of prosthesis 102, in which an artificial ligament 1118 is connected at one end 1121 to the femoral component 1110, and at the other end 1123 to a biasing element 1140 mounted in the stem 1108 of the tibial component 1104. The biasing element 1140 engages the ligament 1118 via a bearing element 1144. The biasing element 1140 and bearing element 1144 are both received within a bore 1126 formed in the stem 1108. The bore 1126 opens onto the bearing surface 1114 of the tibial tray 1106 at a mouth 1130. The mouth 1130 extends partially into the bore 1126 to define an internal annular shoulder 1154 having an annular bearing surface 1156. The mouth 1130 is smooth, widening to accommodate the artificial ligament 1118 with some play. The mouth may be radiused or chamfered. The artificial ligament 1118 extends into the bore 1126 through a space 1127, defined between the bearing components 1112, 1113, so that the artificial ligament 1118 substantially does not interfere with the bearing components 1112 during normal articulation of the prosthesis.

Any convenient means of connection of the end 1121 of the ligament 1118 to the femoral component 1110 is contemplated. For example, a boss or peg 1119 may be formed on the femoral component for attachment of the ligament 1118. The end 1121 of the ligament 1118 may be folded over and glued, sewn or otherwise fixed to form a loop (not shown). Alternatively, a hole or eye may be formed in the end 1121 of the ligament 1118. The artificial ligament may then be secured to the boss 1119 by passing the loop or eye over the boss 1119. The boss 1119 may have an enlarged head and narrower stem to encourage stable fixation of the ligament once attached to the boss 1119.

With reference also to FIG. 18, the other end 1123 of the artificial ligament 1118 is attached to the biasing element 1140 via the bearing element 1144. Any convenient means of connection between the end 1123 of the ligament 1118 and the bearing element 1144 is contemplated. For example, the end 1123 of the ligament 1118 may pass wholly or substantially through the bearing element 1144 and be prevented from passing back through the bearing element 1144 by a stop 1134. The stop 1134 may take the form of an enlarged body, for example a spherical body (as illustrated in FIG. 16), a cylinder, or any other appropriate form. Alternatively, the stop may comprise a knot 1135 formed in the end 1123 of the ligament 1118 (as illustrated in FIG. 17). In an alternative embodiment (not shown) the end 1123 of the ligament 1118 may be attached directly to the bearing element 1144 without passing through the body of the bearing element 1144.

The biasing element 1140 comprises a resilient element 1142. In the illustrated embodiment, the resilient element 1142 is a coiled compression spring 1146 and the bearing element 1144 is a plate 1148. However, the resilient element may consist of or comprise any appropriate spring or springs, for example a Belleville washer or an elastic or elastomeric member. An appropriate bearing element may be selected according to the choice of resilient element.

As illustrated particularly in FIG. 18, the spring 1146 and bearing plate 1148 are received within the bore 1126 of the stem 1108. The artificial ligament 1118 extends into the mouth 1130 of the bore 1126, through the coil spring 1146 and through a passage 1150 formed in the bearing plate 1148. A stop 1134 or knot 1136 prevents the ligament 1118 passing back through the passage 1150 as described above. When tensile forces are applied to the ligament 1118, the knot 1135 or stop 1134 bears against an adjacent surface of the plate 1148, forcing an opposite surface of the plate 1148 to engage and compress the spring 1146 against the annular bearing surface 1152 of the shoulder 1150.

The spring 1146 assists in replicating the natural stiffness of the ligament that is to be replaced. The characteristics of the spring are therefore selected to be similar to those of the natural ACL.

Referring to FIGS. 18 and 19, in a further embodiment of prosthesis 1202, an artificial ligament 1218 is connected at one end 1221 to the femoral component 1210, and at the other end 1223 to a tensioning element 1220 mounted in the stem 1208 of the tibial component 1204. The tensioning element 1220 is cylindrical and formed with an external thread 1222 which engages an internal thread 1224 formed in a bore 1226 in the stem 1208.

As in the embodiment of FIGS. 16 and 17, any convenient means of connection of the end 1221 of the ligament 1218 to the femoral component 1210 is contemplated. For example, a boss or peg 1219 may be formed on the femoral component for attachment of the ligament 1218. The end 1221 of the ligament 1218 may be folded over and glued, sewn or otherwise fixed to form a loop (not shown). Alternatively, a hole or eye may be formed in the end 1221 of the ligament 1218. The artificial ligament may then be secured to the boss 1219 by passing the loop or eye over the boss 1219. The boss 1219 may have an enlarged head and narrower stem to encourage stable fixation of the ligament once attached to the boss 1219.

The other end 1223 of the artificial ligament 1218 is attached to the tensioning element 1220. Again, as in the embodiment of FIGS. 16 and 17, any convenient means of connection between the end 1223 of the ligament 1218 and the tensioning element 1220 is contemplated. For example, the end 1223 of the ligament 1218 may pass wholly or substantially through the tensioning element 1220 and be prevented from passing back through the tensioning element 1220 by a stop 1234. The stop 1234 may take the form of an enlarged body, for example a spherical body (as illustrated in FIG. 18), a cylinder, or any other appropriate form. Alternatively, the stop may comprise a knot 1235 formed in the end 1223 of the ligament 1218 (as illustrated in FIG. 19). In an alternative embodiment (not shown) the end 1223 of the ligament 1218 may be attached directly to the tensioning element 1220 without passing through the body of the tensioning element 1220.

The bore 1226 in which the tensioning element 1220 is received opens onto the bearing surface 1214 of the tibial tray 1206 at a mouth 1230. The mouth 1230 is smooth, widening to accommodate the artificial ligament 1218 with some play. The mouth may be radiused or chamfered. The artificial ligament 1218 extends into the bore 1226 through a space 1227, defined between the bearing components 1212, 1213, so that the artificial ligament 1218 substantially does not interfere with the bearing components 1212 during normal articulation of the prosthesis. In the case of a monoblock bearing component (not shown) a suitable opening is formed to allow passage of the artificial ligament and to minimise wear or abrasion of the ligament 1218 during movement.

As illustrated in FIG. 19, the tensioning element 1220 may have a substantially spherical recess 1229 in its end 1231 closest to the free end 1228 of the stem 128. A passage 1232 extends from a base of the recess through the tensioning element towards the mouth 1230 in the tibial tray. The passage 1232 is large enough to receive the loop, eye or other fixation feature at the end 1221 of the ligament 1218, but is too small to allow the stop 1234 to pass through. Alternatively, as illustrated in FIG. 20, the tensioning element may simply comprise a passage 1232, the stop or knot 1234, 1235 engaging against a surface 1237 of the tensioning element 1220.

With reference to FIG. 21, a further embodiment of knee prosthesis combines features of the last two embodiments. The prosthesis 1302 comprises a tensioning element 1320, substantially as described with reference to the embodiment of FIGS. 18 and 19, and a biasing element 1340, substantially as described with reference to the embodiment of FIGS. 16 and 17. The biasing element 1340 acts between the ligament 1318 and the tensioning element 1320, as opposed to the shoulder 1350 of the embodiment of FIGS. 16 and 17. The biasing element 1340 comprises a resilient element 1342, which engages the ligament 1318 via a bearing element 1344. In the illustrated embodiment, the resilient element 1342 is a coiled compression spring 1346 and the bearing element 1344 is a plate 1348. However, the resilient element may be any appropriate spring or springs, for example a Belleville washer or an elastic or elastomeric member. An appropriate bearing element may be selected according to the choice of resilient element.

As illustrated in FIG. 21, the spring 1346 and bearing plate 1348 are received within the bore 1326 of the stem 1308 beneath the tensioning element 1320. The artificial ligament 1318 extends through the passage 1332 in the tensioning element, through the coil spring 1346 and through a passage 1350 formed in the bearing plate 1348. A stop 1334 or knot 1336 is formed on the end 1323 of the ligament 1318 as described above. The knot 1335 or stop 1334 prevents the ligament 1318 passing back through the passage 1350. When tensile forces are applied to the ligament 1318, the knot 1335 or stop 1334 bears against an adjacent surface of the plate 1348, forcing an opposite surface of the plate 1348 to engage and compress the spring 1346 against the adjacent surface of the tensioning element 1320.

The spring assists in replicating the natural stiffness of a ligament. The characteristics of the spring are selected accordingly to be similar to those of the natural ACL.

Implantation of the prosthesis of the present invention will be described with reference to the embodiment of FIG. 20. However, it will be understood that corresponding techniques may be employed for all embodiments disclosed herein.

In use of the prosthesis 1302, the femoral component 1310 is implanted into a distal end of a femur (not shown) and the tibial component 1304 is implanted into a proximal end of a tibia (not shown), such that the stem 1308 is located in the intramedulary canal of the tibia, and the tibial tray 1306 rests on the resected proximal end of the tibia. The appropriate bearing components) are placed between the femoral component 1310 and the tibial component 1304.

The artificial ligament 1318, compression spring 1346 and bearing plate 1348, tensioning element 1320 and tibial component 1304 are preassembled prior to implantation. The ligament 1318 is connected to the tensioning element 1320 by passing the end 1321 of the ligament 1318 through the passage 1332 via the passage 1350 in the bearing plate 1348 and the spring 1346 and feeding the ligament 1318 through the passage 1332 until the stop 1334 or knot 1335 engages a surface of the bearing plate 1348. The tensioning element 1320 is then screwed to an appropriate depth into the bore 1326 in the tibial component 1304 to achieve initial tensioning of the ligament 1318 when fully connected.

The femoral and tibial components 1310, 1304 are then implanted using standard techniques. Once the tibial component 1304 is implanted, the free end 1321 of the ligament 1318 projects through the mouth 1330 in the tibial tray towards the femoral component 1310. The appropriate bearing components are then placed between the femoral component 1310 and the tibial component 1304 in a known manner.

The end 1121 of the ligament 1118 is then attached to the femoral component 1110 by passing the loop or eye over the boss 1119.

The joint is then examined to determine whether the tension in the artificial ligament 1318 is balanced with the tension in the retained posterior cruciate ligament (PCL). If the tension in the artificial ligament 1318 is balanced with that in the PCL, the implantation procedure is complete. If the tension in the artificial ligament 1318 is not balanced with that in the PCL, the position of the tensioning element 1320 within the bore 1326 is adjusted, so as to increase or reduce the tension applied to the ligament 1318. A tool (not shown) may be inserted through the mouth 1330 to engage a drive formation (not shown) formed on the tensioning element 1320. By rotating the tool, the tensioning element 1320 is rotated and moves axially along the internal thread in the bore 1326, thereby adjusting the tension in the artificial ligament 1318.

With reference to FIGS. 17 to 20, the embodiments of the present invention may further comprise a ligament support 1160 that is operable to change the line of action of the artificial ligament 1118. The ligament support may comprise a section of or a projection from the mouth 1130 of the bore 1126 in the tibial component 1114. Alternatively, as shown in FIG. 21, the ligament support may comprise a lug 1070 that projects from the surface 1014 of the tibial tray 1006. The lug may be integrally formed with or connected to the tibial tray 1006.

FIG. 22 shows a knee prosthesis comprising a tibial component 1004 having a tibial tray 1006 integrally formed with a stem 1008. A pair of bearing components 2012, 2013 separate the tibial component 1004 from a femoral component (not shown) and are formed with bearing surfaces which engage a corresponding bearing surface 1014 on the tibial tray 1006. The bearing components 2012, 2013 are interconnected by a linking element 2008, as described with reference to the embodiment of FIGS. 1 and 2. A retaining element in the form of bridge element 2050 is fixed to the tibial tray 1006 to limit the motion of the linking element 2008. The bridge element 2050 comprises a beam 2052 and two supporting legs 2054, 2056. The beam 2052 extends substantially parallel to the proximal surface of the tibial tray 1006 in an anterior-posterior direction and spans substantially the entire width of the tibial tray 1006. The supporting legs 2054, 2056 are positioned approximately at the anterior and posterior edges of the tray 1006, substantially equidistantly at the medial and lateral edges of the tray 1006. The bridge element 2050 thus divides the tibial tray 1006 into its lateral and medial compartments and defines a passage 2060 therebetween, which accommodates the linking element 2008.

An artificial ligament (not shown) is connected to a biasing element (not shown) housed in the stem 1008. As in previous embodiments incorporating a ligament, the ligament passes out of an opening 1030 in the tibial tray 1006 and abuts a side of the beam 2052 of the bridge element 2050. It will be appreciated that the engagement of the ligament with the side of the bridge element 2050 causes a deflection of the ligament and a change in the line of action of the ligament. In order to avoid fretting or other wear related damage of the ligament in use, the bridge element 2050 is provided with a recess or chamfer 2051 which helps to locate the ligament, avoids dislocation and provides a smooth surface of engagement between the bridge element 2050 and the ligament. Thus, the bridge element 2050 has the dual function of limiting the motion of the bearing components 2012, 2013 and acting as a ligament support to change the line of action of the artificial ligament. In alternative embodiments not illustrated, the bridge element 2050 may comprise a pulley or may be provided with a projection or boss to assist in aligning the ligament and preventing dislocation. Furthermore the ligament support surface formed on the bridge element 2050 may be polished or otherwise surface finished to reduce wear of the artificial ligament.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

The invention claimed is:

1. A method of implanting a prosthesis having first and second bone engaging elements, an artificial ligament, and an adjustable tensioning element operatively coupled to a first end of the artificial ligament and to the first bone engaging element, the first bone engaging element including a lateral compartment and a medial compartment, the method comprising:
   selecting the height of each of the lateral and medial compartments according to natural positions of lateral and medial bearing surfaces of a healthy tibia;
   assembling the first bone engaging element, adjustable tensioning element and artificial ligament;
   implanting the first and second bone engaging elements into bone tissue;
   connecting a second end of the artificial ligament to the second bone engaging element; and
   adjusting the position of the adjustable tensioning element until a predetermined tension within the artificial ligament is achieved.

2. The method as claimed in claim 1, wherein the first bone engaging component comprises a tibial component and the second bone engaging component comprises a femoral component.

3. The method as claimed in claim 2, further comprising mounting the tibial component onto a resected proximal surface of a tibia.

4. The method as claimed in claim 3, wherein the tibial component comprises a tray and a stem, wherein a distal surface of the tray is mounted onto the resected proximal surface of the tibia and wherein the stem is located in an intramedulary canal of the tibia.

5. The method as claimed in claim 4, further comprising attaching the femoral component to a distal surface of a femur.

6. The method as claimed in claim 1, wherein the second end of the artificial ligament is connected to the second bone engaging component by a boss or a peg formed on the second bone engaging component.

7. The method as claimed in claim 6, further comprising folding the second end of the artificial ligament over and fixing to form a loop, wherein the artificial ligament is connected to the second bone engaging component by passing the loop over the boss or peg.

8. The method as claimed in claim 6, further comprising forming a hole in the second end of the artificial ligament and connecting the artificial ligament to the second bone engaging component by passing the hole over the boss or peg.

9. The method as claimed in claim 1, further comprising determining whether the tension in the artificial ligament is balanced with the tension in a posteria cruciate ligament and, if the tension in the artificial ligament is not balanced with the tension in the posteria cruciate ligament, adjusting the position of the tensioning element.

10. A method for implanting a knee joint prosthesis having a femoral component, a tibial component, an artificial ligament and a tensioning element, the method comprising:
    implanting the tibial component having the artificial ligament and tensioning element coupled thereto on a proximal surface of a tibia;
    implanting the femoral component on a distal surface of a femur;
    connecting the artificial ligament to the femoral component; and
    adjusting a position of the tensioning element relative to the tibial component to adjust a tension in the artificial ligament, wherein adjusting the position of the tensioning element relative to the tibial component further includes threadably moving the tensioning element relative to the tibial component.

11. The method as claimed in claim 10, wherein adjusting the position of the tensioning element further includes adjusting the tensioning element until a predetermined tension within the artificial ligament is achieved.

12. The method as claimed in claim 10, wherein connecting the artificial ligament to the femoral component further includes connecting a loop of the artificial ligament to a boss or a peg on the femoral component.

13. The method as claimed in claim 10, further comprising determining whether the tension in the artificial ligament is balanced with the tension in a posteria cruciate ligament and, if the tension in the artificial ligament is not balanced with the tension in the posteria cruciate ligament, adjusting the position of the tensioning element.

14. The method as claimed in claim 10, further comprising positioning a medial bearing component and a lateral bearing component coupled together by a linking element between the femoral component and the tibial component.

15. The method as claimed in claim 14, further comprising positioning a bridge coupled to a tibial tray of the tibial component over the linking element to limit motion of the linking element, medial bearing component, and lateral bearing component between the femoral component and the tibial component.

16. A method of implanting a prosthesis having first and second bone engaging elements, an artificial ligament, and an adjustable tensioning element operatively coupled to a first end of the artificial ligament and to the first bone engaging element, the first bone engaging component including a lateral compartment and a medial compartment, the method comprising:
    determining a height of each of the lateral and medial compartments via kinematic analysis of a patient;
    assembling the first bone engaging element, adjustable tensioning element, and artificial ligament;
    implanting the first and second bone engaging elements into bone tissue;
    connecting a second end of the artificial ligament to the second bone engaging element; and
    adjusting the position of the adjustable tensioning element until a predetermined tension within the artificial ligament is achieved.

17. The method as claimed in claim 16, wherein the first bone engaging element comprises a tibial component and the second bone engaging element comprises a femoral component.

18. The method as claimed in claim 17, further comprising mounting the tibial component onto a resected proximal surface of a tibia.

19. The method as claimed in claim 18, wherein the tibial component comprises a tray and a stem, wherein a distal surface of the tray is mounted onto the resected proximal surface of the tibia and wherein the stem is located in an intramedulary canal of the tibia.

20. The method as claimed in claim 19, further comprising attaching the femoral component to a distal surface of a femur.

* * * * *

UNITED STATES PATENT AND TRADEMARK OFFICE
CERTIFICATE OF CORRECTION

PATENT NO. : 9,675,441 B2  
APPLICATION NO. : 14/666614  
DATED : June 13, 2017  
INVENTOR(S) : Wolfson et al.

Page 1 of 1

It is certified that error appears in the above-identified patent and that said Letters Patent is hereby corrected as shown below:

In the Claims

In Column 16, Line 53, in Claim 1, delete "element" and insert --element,-- therefor In Column 17, Line 5, in Claim 4, delete "intramedulary" and insert --intramedullary-- therefor In Column 17, Line 26, in Claim 9, delete "posteria" and insert --posterior-- therefor In Column 17, Line 28, in Claim 9, delete "posteria" and insert --posterior-- therefor In Column 17, Line 34-35, in Claim 10, delete "ligament" and insert --ligament,-- therefor In Column 18, Line 5, in Claim 13, delete "posteria" and insert --posterior-- therefor In Column 18, Line 7, in Claim 13, delete "posteria" and insert --posterior-- therefor In Column 18, Line 47, in Claim 19, delete "intramedulary" and insert --intramedullary-- therefor Signed and Sealed this
Seventeenth Day of April, 2018

Andrei Iancu
*Director of the United States Patent and Trademark Office*